United States Patent
Kim et al.

(10) Patent No.: US 9,292,975 B2
(45) Date of Patent: Mar. 22, 2016

(54) SYSTEM AND METHOD FOR MONITORING VIBRATION DATA

(71) Applicant: HONEYWELL INTERNATIONAL INC., Morristown, NJ (US)

(72) Inventors: Kyusung Kim, Plymouth, MN (US); Chris Hickenbottom, Phoenix, AZ (US); David Daniel Lilly, Ramona, CA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 22 days.

(21) Appl. No.: 13/961,549

(22) Filed: Aug. 7, 2013

(65) Prior Publication Data

US 2015/0046059 A1    Feb. 12, 2015

(51) Int. Cl.
*G07C 5/00* (2006.01)
*G01H 1/00* (2006.01)
*G01M 15/12* (2006.01)
*G01N 19/08* (2006.01)

(52) U.S. Cl.
CPC .................. *G07C 5/00* (2013.01); *G01H 1/003* (2013.01); *G01M 15/12* (2013.01); *G01N 19/08* (2013.01)

(58) Field of Classification Search
CPC ......... G07C 5/00; G01H 1/003; G01M 15/12; G01N 19/08
See application file for complete search history.

(56) References Cited

U.S. PATENT DOCUMENTS

| | | | |
|---|---|---|---|
| RE31,750 E | 11/1984 | Morrow | |
| 5,069,071 A | 12/1991 | McBrien et al. | |
| 5,922,963 A | 7/1999 | Piety et al. | |
| 6,208,944 B1 | 3/2001 | Franke et al. | |
| 6,526,831 B2 | 3/2003 | Ben-Romdhane | |
| 7,487,679 B2 | 2/2009 | Sirrine et al. | |
| 7,559,240 B2 | 7/2009 | Iwatsubo et al. | |
| 8,219,361 B2 | 7/2012 | Leigh | |
| 2003/0200014 A1* | 10/2003 | Remboski | G01M 13/028 701/33.9 |

* cited by examiner

*Primary Examiner* — Yonel Beaulieu
*Assistant Examiner* — Basil T Jos
(74) *Attorney, Agent, or Firm* — Ingrassia Fisher & Lorenz, P.C.

(57) ABSTRACT

A system and method are provided for monitoring vibration data. A vehicle, for example, may include at least one engine component, a sensor coupled to the at least one engine component and configured to monitor a vibration of the at least one engine component, and a processor communicatively coupled to the sensor, the processor configured to determine a plurality of envelope spectrums based upon vibration data from the sensor, determine fault frequencies for each of the at least one engine component based upon a rotating speed of each of the at least one components, and monitor each envelope spectrum for changes at the determined fault frequencies.

17 Claims, 3 Drawing Sheets

SYSTEM AND METHOD FOR MONITORING VIBRATION DATA

STATEMENT REGARDING FEDERALLY SPONSORED RESEARCH OR DEVELOPMENT

This invention was made with Government support under Agreement No. W911W6-08-0001 awarded by the Army (AATE) Program. The Government has certain rights in this invention.

TECHNICAL FIELD

The present disclosure generally relates to health monitoring, and more particularly relates to a system and method for monitoring vibration data.

BACKGROUND

A mechanical health monitoring system for rotating machinery has two primary objectives. One primary objective is issuing an advance warning of an impending failure. The other primary objective is preventing mission aborts and costly repairs due to primary and secondary damage. The advance warning period mentioned in the first objective can be extended by either detecting damage early and with high confidence or by delaying the end of life as late as possible. Therefore what is needed is automated continuous monitoring of the mechanical health of the rotating equipment to detect a damage as early as possible to allow enough time to schedule a repair.

BRIEF SUMMARY

In one embodiment, for example, a vehicle is provided. The vehicle may include, but is not limited to at least one engine component, a sensor coupled to the at least one engine component and configured to monitor a vibration of the at least one engine component, and a processor communicatively coupled to the sensor, the processor configured to determine a plurality of envelope spectrums based upon vibration data from the sensor, determine fault frequencies for each of the at least one engine component based upon a rotating speed of each of the at least one components, and monitor each envelope spectrum for changes at the determined fault frequencies.

In another embodiment, a method for monitoring health of a vehicle is provided. The method may include, but is not limited to receiving, by a processor, vibration data from a vibration sensor, determining, by the processor, a plurality of envelope spectrums to be analyzed based upon the vibration data, determining, by the processor, a plurality of fault frequencies based upon a rotational speed of at least one engine component of the vehicle, and monitoring, by the processor, the plurality of fault frequencies within each of the plurality of envelope spectrums.

In yet another embodiment, a computer-readable medium is provided. The computer-readable medium, which when executed by a processor, cause the processor to determine a plurality of envelope spectrums based upon vibration data from a sensor, determine fault frequencies for at least one engine component based upon a rotating speed of each of the at least one components, and monitor each envelope spectrum for changes at the determined fault frequencies.

BRIEF DESCRIPTION OF THE DRAWINGS

The detailed description will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
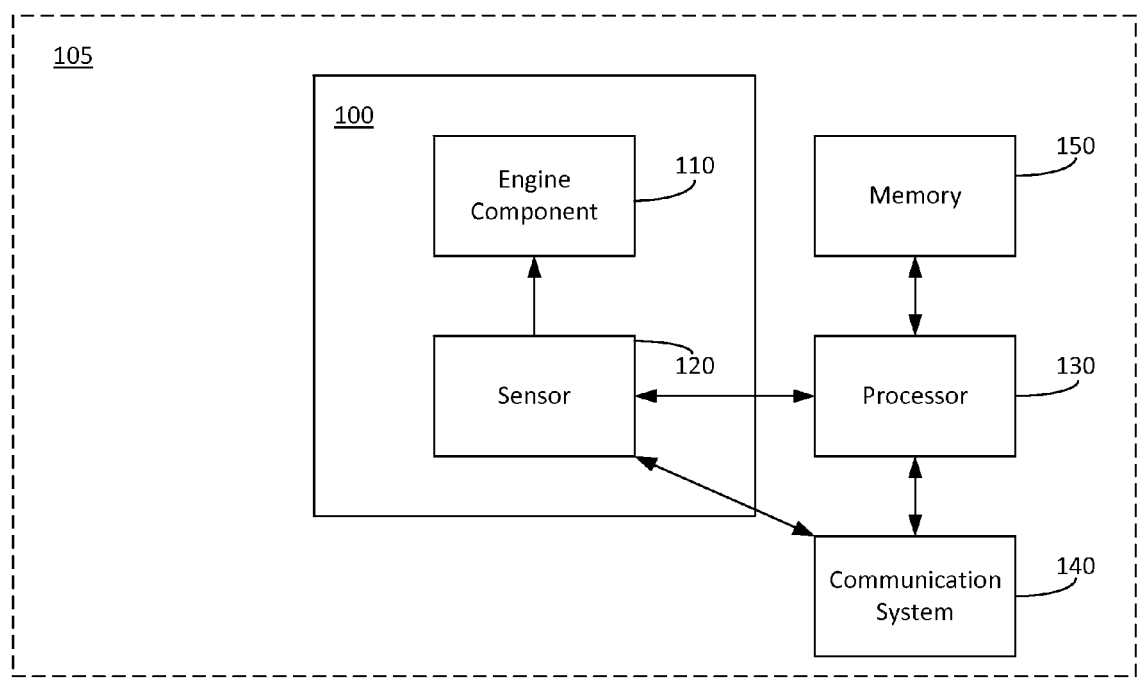
FIG. 1 is a block diagram of an engine, in accordance with an embodiment.

FIG. 1 is a block diagram of an engine 100, in accordance with an embodiment. The engine 100 may be an engine for a vehicle, such as an aircraft, a spacecraft, an automobile, or a marine vehicle, gearboxes, such as helicopter gearboxes, or for a power generator using wind, hydro, or thermal energy, illustrated via block 105. In one embodiment, for example, the engine 100 may be a turbine engine for an aircraft. However, one of ordinary skill in the art would recognize that the engine 100 may utilize other technologies if so desired. The engine 100 includes at least one engine component 110 for which vibration information can indicate damage to the engine component. In one embodiment, for example, the engine component 110 may be a bearing. In other embodiments, for example, the engine component 110 may be gears, shafts, gerotors, cams, any other oil-wetted component, or any combination thereof.

At least one vibration sensor 120 is coupled to the engine 100 proximate to the engine component 110. The vibration sensor(s) 120 collects vibration data from the engine component 110. A processor 130 is communicatively coupled to the vibration sensor 120 and is configured to monitor the health of the vehicle based on information obtained from the vibration sensor 120, as described in further detail below. In one embodiment, for example, the vibration sensor 120 may be configured to transmit sensor data to the processor 130 in real time or in a periodic fashion. In other embodiments, for example, the processor 130 may poll the vibration sensor 120 for data in real time or in a periodic fashion. The processor is configured to analyze the sensor data, as discussed in further detail below.

In one embodiment, for example, the processor 130 may be located in the vehicle 105. The processor 130 could be located anywhere in the vehicle 105, including the engine 100. The processor 130 may be a processor dedicated to analyzing the vibration sensor data, or may be part of other systems in the vehicle 105. In one embodiment, for example, the processor 130 is coupled to a communications system 140 to communicate the results of the vibration analysis to, for example, maintenance personnel. The communication system 140 may utilize any type of data connection including, but not limited to, a cellular data connection, a satellite data connection, a Wi-Fi data connection, a local area network (LAN) data connection, a Bluetooth data connection, or any other data connection or combination thereof.

In another embodiment, for example, the processor 130 for analyzing the vibration data may be located remotely from the vehicle 105. In this embodiment, for example, the vibration sensor 120 and processor 130 may be communicatively coupled via the communication system 140.

In one embodiment, for example, the processor is communicatively coupled to a memory 150. The memory 150 may be any type of non-volatile memory. The memory may store geometry data for each engine component 110 which may be used to determine fault frequencies for each engine component, as discussed in further detail below. While the memory 150 is illustrated as being located in the vehicle in FIG. 1, the memory may also be located remotely. In this embodiment, for example, the processor 130 would communicate with the memory 150 via the communication system 140. In one embodiment, for example, the memory may store instructions, which when executed by the processor, monitor the health of the vehicle as discussed in further detail below.

Figure 2:
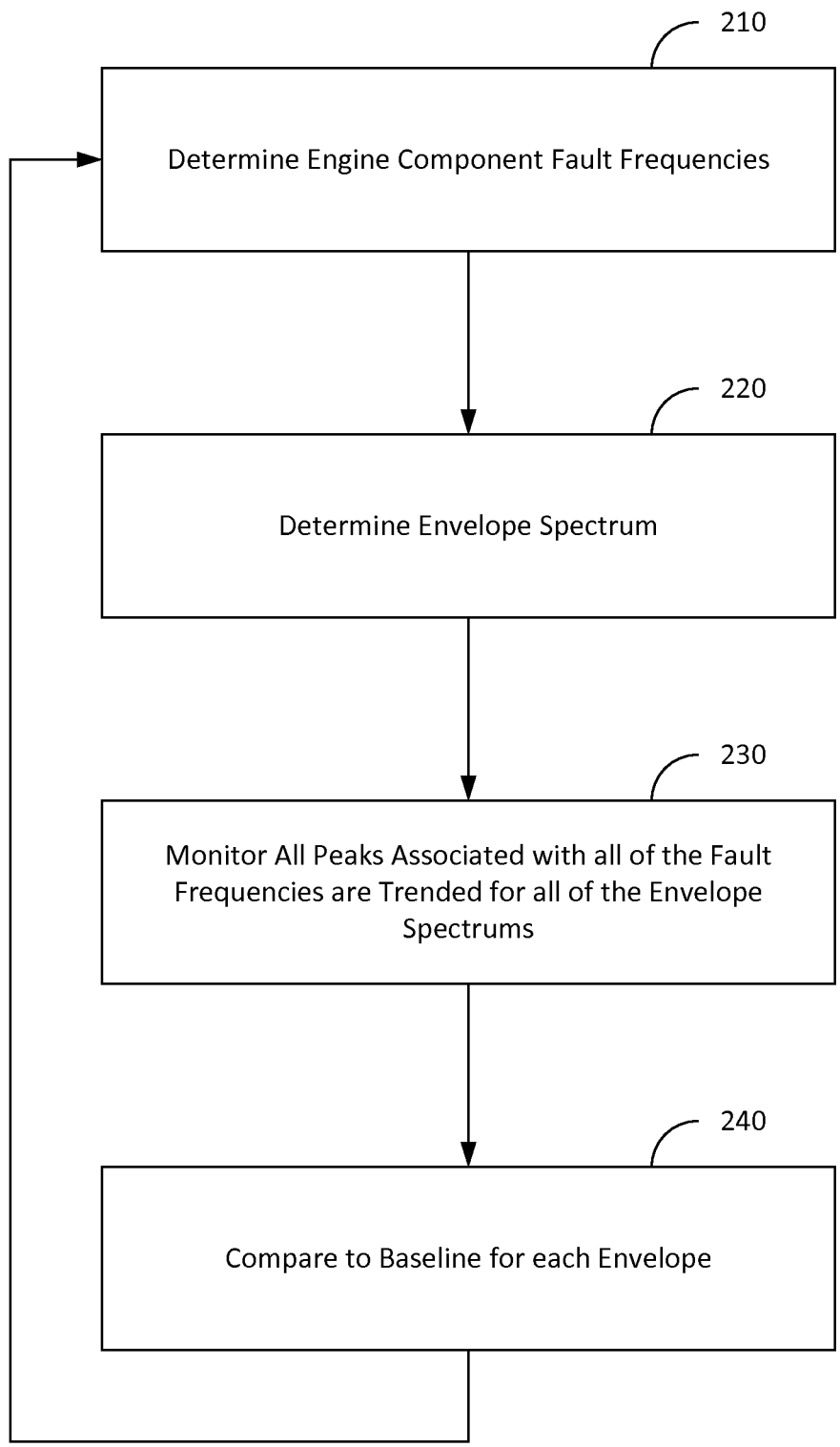
FIG. 2 is a flow diagram illustrating an exemplary method for monitoring the health of an engine in accordance with an embodiment.

FIG. 2 is a flow diagram illustrating an exemplary method 200 for monitoring the health of an engine in accordance with an embodiment. A processor, such as the processor 130 illustrated in FIG. 1, determines one or more fault frequencies for each engine component of interest. (Step 210). The fault frequencies are frequencies at which the respective engine component will vibrate when the engine component is damaged or below optimal/acceptable tolerances or conditions, such as excessive wear. The fault frequencies may be based upon the geometry for each engine component. The fault frequencies may also be based upon the rotating speed of the engine component and/or the engine itself, as a frequency caused by a fault in an engine component would vary depending upon the rotating speed of the engine component and/or the engine itself. The geometry of a bearing, for example, could include, but is not limited to, a number of rolling elements, a rolling element diameter, a pitch diameter and a contact angle. Geometries and fault frequencies for meshing gears could be determined by gear type (straight, bevel, spiral bevel), number of teeth on driver & driven gears, and fault degradation/fault progression. The processor then, based upon the rotating speed of the engine/engine component, determines the one or more fault frequencies for each engine component of interest. In a bearing, for example, the processor could determine a ball pass frequency for an inner race, a ball pass frequency for an outer race, a ball spin frequency and a fundamental train frequency.

The processor than determines envelope spectrums for which to conduct the analysis. (Step 220). While all of the fault frequencies may be within a range, for example, between 9 kilohertz (kHz) and 24 kHz, performing a single analysis over the entire frequency range may make it difficult for the processor to distinguish frequencies due to low signal to noise ratio (signal in this case being defines as the fault frequencies of interest and noise being defined as all other energy not associated with the signal of interest). Accordingly, the processor determines a plurality of envelope spectrums (i.e., smaller frequency ranges) to perform the analysis over. The envelope spectrums may be based upon a minimum resonant frequency of the raw vibration data from the vibration sensor, a maximum resonant frequency of the raw vibration data from the vibration sensor, a minimum bandwidth envelope window, a maximum bandwidth envelope window, and a step size for a variable length of the bandwidth window. If, for example, the minimum resonant frequency is 9 kHz, the maximum resonant frequency is 24 kHz, the step size for a variable resonant frequency is 1 kHz, the minimum bandwidth envelope window is 6 kHz, the maximum bandwidth envelope window is 11 kHz and the a step size for a variable length of the bandwidth window is 1 kHz, the envelope spectrums (in kHz) would be: [9-15], [9-16], [9-17], [9-18], [9-19], [9-20], [10-16], [10-17], [10-18], [10-19], [10-20], [10-21], [11-17] [11-18], [11-19], [11-20], [11-21], [11-22], [12-18], [12-19], [12-20], [12-21], [12-22], [12-23], [13-19], [13-20], [13-21], [13-22], [13-23], [13-24], [14-20], [14-21], [14-22], [14-23], [14-24], [15-21], [15-22], [15-23], [15-24], [16-22], [16-23], [16-24], [17-23], [17-24], and [18-24]. In this example, there are forty-five envelope spectrums representing forty-five frequency ranges over which the processor will analyze the vibration data. By breaking up the total frequency range (i.e., the minimum resonant frequency to the maximum resonant frequency) into a series of smaller envelope spectrums, change in frequency trends become more apparent. Accordingly, the processor can determine faults quicker and more accurately.

The processor then, for each of the envelope spectrums, monitors and tracks the peak amplitude corresponding to the fault frequencies for each engine component of interest. (Step 230). According, using the example above, if there were ten components of interest, each with four fault frequencies (i.e., a total of forty frequencies of interest), and forty-five frequency envelopes, the processor could be monitoring up to one-thousand eight-hundred frequencies for each pass through the method 200. However, this assumes that there were no overlapping frequencies of interest and that all of the frequencies of interest were in each envelope, which is unlikely to occur.

The processor then compares the frequencies of interest in each monitored envelope spectrum to previous envelope spectrums and/or a baseline spectrum. (Step 240). By comparing each envelope spectrum with previous envelope spectrums and/or a baseline spectrum, each envelope spectrum having a different frequency range, as discussed above, changes in the envelope spectrum are more apparent. If a change in a peak of one or more of the frequencies of interest changes more than a predetermined threshold, the processor can then issue a maintenance warning. The processor then returns to step 210 and 220 and recomputes the envelope spectrum, if necessary (i.e., the rotational speed of one of the engine components has changed and thus the corresponding fault frequencies have changed which could raise or lower the minimum or maximum resonant frequency detected by the vibration sensors), and then continues to monitor the computed envelope spectrums, as discussed above.

Figure 3:
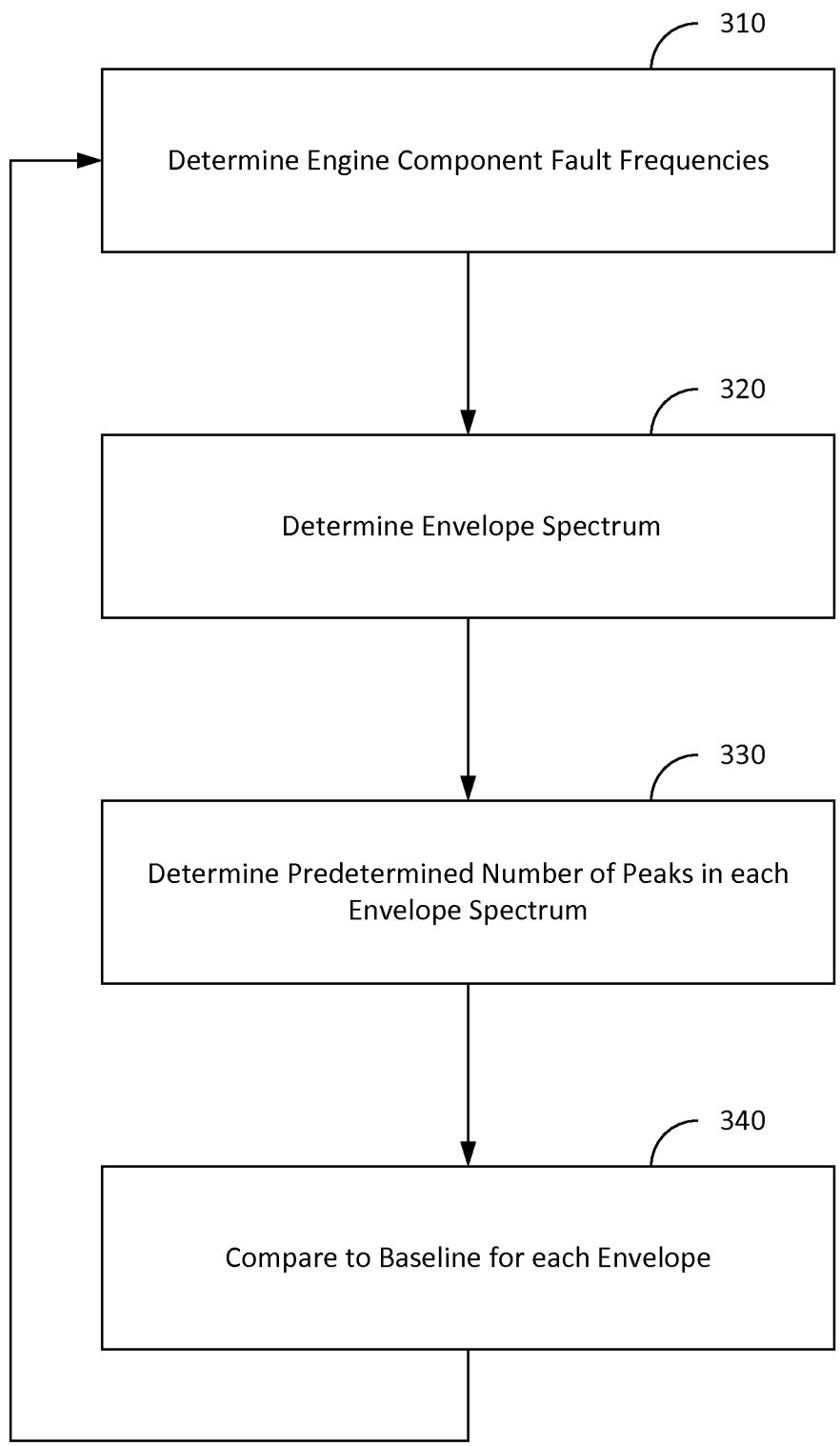
FIG. 3 is a flow diagram illustrating another exemplary method for monitoring the health of an engine in accordance with an embodiment.

FIG. 3 is a flow diagram illustrating another exemplary method 300 for monitoring the health of an engine in accordance with an embodiment. A processor, such as the processor 130 illustrated in FIG. 1, determines one or more fault frequencies for each engine component of interest. (Step 310). The fault frequencies may be based upon the geometry for each engine component. The fault frequencies may also be based upon the rotating speed of the engine component and/or the engine itself, as a frequency caused by a fault in an engine component would vary depending upon the rotating speed of the engine component and/or the engine itself. The geometry of a bearing, for example, could include, but is not limited to, a number of rolling elements, a rolling element diameter, a pitch diameter and a contact angle. The processor then, based upon the rotating speed of the engine/engine component, determines the one or more fault frequencies for each engine component of interest. In a bearing, for example, the processor could determine a ball pass frequency for an inner race, a ball pass frequency for an outer race, a ball spin frequency and a fundamental train frequency.

The processor than determines envelope spectrums for which to conduct the analysis. (Step 320). While all of the fault frequencies may be within a range, for example, between 9 kilohertz (kHz) and 24 kHz, performing a single analysis over the entire frequency range may make it difficult for the processor to distinguish frequencies due to faults from noise. Accordingly, the processor determines a plurality of envelope spectrums (i.e., smaller frequency ranges) to perform the analysis over. The envelope spectrums may be based upon a minimum resonant frequency of the raw vibration data from the vibration sensor, a maximum resonant frequency of the raw vibration data from the vibration sensor, a step size for a variable resonant frequency, a minimum bandwidth envelope window, a maximum bandwidth envelope window, and a step size for a variable length of the bandwidth window. If, for example, the minimum resonant frequency is 9 kHz, the maximum resonant frequency is 24 kHz, the step size for a variable resonant frequency is 1 kHz, the minimum bandwidth envelope window is 6 kHz, the maximum bandwidth envelope window is 11 kHz and the a step size for a variable length of the bandwidth window is 1 kHz, the envelope spectrums (in kHz) would be: [9-15], [9-16], [9-17], [9-18], [9-19], [9-20], [10-16], [10-17], [10-18], [10-19], [10-20], [10-21], [11-17] [11-18], [11-19], [11-20], [11-21], [11-22], [12-18], [12-19], [12-20], [12-21], [12-22], [12-23], [13-19], [13-20], [13-21], [13-22], [13-23], [13-24], [14-20], [14-21], [14-22], [14-23], [14-24], [15-21], [15-22], [15-23], [15-24], [16-22], [16-23], [16-24], [17-23], [17-24], and [18-24]. In this example, there are forty-five envelope spectrums representing forty-five frequency ranges over which the processor will analyze the vibration data. By breaking up the total frequency range (i.e., the minimum resonant frequency to the maximum resonant frequency) into a series of smaller envelope spectrums, change in frequency trends become more apparent. Accordingly, the processor can determine faults quicker and more accurately.

The processor then, for each of the envelope spectrums, determines a predetermined number of peak frequencies. (Step 330). For example, if the predetermined number is ten, the processor would determine the frequency of the ten highest peaks in each envelope spectrum. According, using the example above, if there were ten components of interest, each with four fault frequencies (i.e., a total of forty frequencies of interest), and forty-five frequency envelopes, the processor would be monitoring four-hundred and fifty frequencies in each pass through the method 300.

The processor then compares each monitored envelope spectrum to a baseline spectrum and/or a previously monitored corresponding envelope spectrum. (Step 340). By comparing each envelope spectrum with a baseline spectrum and/or a previously monitored corresponding envelope spectrum, each envelope spectrum having a different frequency range, as discussed above, changes in the envelope spectrum are more apparent. Accordingly, if a peak changes in any one of the envelope spectrums and the peak is near one of the frequencies of interest (or a related frequency such as a harmonic frequency or sideband frequency), the processor can then issue a maintenance warning. The processor then returns to steps 310 and 320 and recomputes the envelope spectrum, if necessary (i.e., the rotational speed of one of the engine components has changed and thus the corresponding fault frequencies), and then continues to monitor the computed envelope spectrums, as discussed above.

Those of skill in the art will appreciate that the various illustrative logical blocks, modules, circuits, and algorithm steps described in connection with the embodiments disclosed herein may be implemented as electronic hardware, non-transitory computer readable medium, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A vehicle, comprising:
   at least one engine component;
   a sensor coupled to the at least one engine component and configured to monitor a vibration of the at least one engine component; and
   a processor communicatively coupled to the sensor, the processor configured to:
      determine a plurality of envelope spectrums based upon vibration data from the sensor;
      determine fault frequencies for each of the at least one engine component based upon a rotating speed of each of the at least one engine component; and
      monitor each envelope spectrum for changes at the determined fault frequencies,
      wherein the processor is further configured to determine the plurality of envelope spectrums based upon a minimum resonant frequency of the vibration data, a maximum resonant frequency of the vibration data, a step size for variable resonant frequency, a minimum bandwidth for an envelope window, a maximum bandwidth for the envelope window, and a step size for variable length of bandwidth.

2. The vehicle of claim 1, wherein the processor is further configured to monitor each envelope spectrum for changes at the determined fault frequencies by monitoring each fault frequency in each envelope spectrum and comparing a currently monitored envelope spectrum with a baseline envelope spectrum.

3. The vehicle of claim 2, wherein the processor is further configured to compare the currently monitored envelope spectrum with a previously monitored envelope spectrum.

4. The vehicle of claim 1, wherein the processor is further configured to monitor each envelope spectrum for changes at the determined fault frequencies by determining a predetermined number of peaks in each currently monitored envelope spectrum and, when one of the predetermined peaks corresponds to one of the fault frequencies, comparing the corresponding peak from the currently monitored envelope spectrum to a baseline envelope spectrum.

5. The vehicle of claim 1, wherein the processor is further configured to compare the corresponding peak from a currently monitored envelope spectrum to a previously monitored envelope spectrum.

6. The vehicle of claim 1, wherein the at least one engine component includes a bearing.

7. The vehicle of claim 1, wherein the processor is further configured to monitor sideband frequencies corresponding to the determined fault frequencies.

8. A method for monitoring health of a vehicle, comprising:
   receiving, by a processor, vibration data from a vibration sensor coupled to at least one engine component of the vehicle;
   determining, by the processor, a plurality of envelope spectrums to be analyzed based upon a minimum resonant frequency of the vibration data, a maximum resonant frequency of the vibration data, a step size for variable resonant frequency, a minimum bandwidth for an envelope window, a maximum bandwidth for the envelope window, and a step size for variable length of bandwidth;
   determining, by the processor, a plurality of fault frequencies based upon a rotational speed of the at least one engine component of the vehicle; and
   monitoring, by the processor, the plurality of fault frequencies within each of the plurality of envelope spectrums.

9. The method of claim 8, wherein the monitoring further comprises:
   determining a predetermined number of peaks in each of the plurality of envelope spectrums; and
   tracking at least one of the predetermined peaks when the at least one of the predetermined peeks corresponds to one of the plurality of fault frequencies.

10. The method of claim 9, wherein the tracking further comprises comparing the at least one of the predetermined peaks to one of a baseline envelope spectrum.

11. The method of claim 9, wherein the tracking further comprises comparing the at least one of the predetermined peaks a previously monitored envelope spectrum.

12. The method of claim 8, wherein the monitoring further comprises tracking, in each of the plurality of envelope spectrums, each of the plurality of fault frequencies within the envelope spectrum.

13. The method of claim 12, wherein the tracking further comprises comparing the at least one of the predetermined peaks to one of a baseline envelope spectrum.

14. The method of claim 12, wherein the tracking further comprises comparing the at least one of the predetermined peaks a previously monitored envelope spectrum.

15. A non-transitory computer-readable medium which when executed by a processor cause the processor to:
   determine a plurality of envelope spectrums based upon a minimum resonant frequency of the vibration data, a maximum resonant frequency of the vibration data, a step size for variable resonant frequency, a minimum bandwidth for an envelope window, a maximum bandwidth for the envelope window, and a step size for variable length of bandwidth;
   determine fault frequencies for at least one engine component based upon a rotating speed of each of the at least one engine component; and
   monitor each envelope spectrum for changes at the determined fault frequencies.

16. The non-transitory computer-readable medium of claim 15, which when executed by the processor further cause the processor to monitor each envelope spectrum for changes at the determined fault frequencies by monitoring each fault frequency in each envelope spectrum and comparing a currently monitored envelope spectrum with a baseline envelope spectrum.

17. The non-transitory computer-readable medium of claim 15, which when executed by the processor further cause the processor to monitor each envelope spectrum for changes at the determined fault frequencies by determining a predetermined number of peaks in each currently monitored envelope spectrum and, when one of the predetermined peaks corresponds to one of the fault frequencies, comparing the corresponding peak from the currently monitored envelope spectrum to a baseline envelope spectrum.

\* \* \* \* \*

UNITED STATES PATENT AND TRADEMARK OFFICE
CERTIFICATE OF CORRECTION

| | | |
|---|---|---|
| PATENT NO. | : 9,292,975 B2 | Page 1 of 1 |
| APPLICATION NO. | : 13/961549 | |
| DATED | : March 22, 2016 | |
| INVENTOR(S) | : Kyusung Kim et al. | |

It is certified that error appears in the above-identified patent and that said Letters Patent is hereby corrected as shown below:

In the Claims

Column 8, line 32, "peeks" should be changed to --peaks--

Signed and Sealed this
Sixteenth Day of August, 2016

Michelle K. Lee
*Director of the United States Patent and Trademark Office*